(12) United States Patent
Hoffnagle et al.

(10) Patent No.: US 8,982,352 B1
(45) Date of Patent: Mar. 17, 2015

(54) REGULAR, STABLE OPTICAL FREQUENCY SCALE FOR CAVITY ENHANCED OPTICAL SPECTROSCOPY

(71) Applicant: Picarro, Inc., Santa Clara, CA (US)

(72) Inventors: John A. Hoffnagle, San Jose, CA (US);
Sze Meng Tan, Sunnyvale, CA (US);
Chris W. Rella, Sunnyvale, CA (US)

(73) Assignee: Picarro, Inc., Santa Clara, CA (US)

( * ) Notice: Subject to any disclaimer, the term of this patent is extended or adjusted under 35 U.S.C. 154(b) by 0 days.

(21) Appl. No.: 14/037,908

(22) Filed: Sep. 26, 2013

Related U.S. Application Data (60) Provisional application No. 61/833,807, filed on Jun. 11, 2013.

(51) Int. Cl.
| | |
|---|---|
| *G01N 21/61* | (2006.01) |
| *G01N 21/25* | (2006.01) |
| *G01J 3/28* | (2006.01) |
| *G01N 21/39* | (2006.01) |
| *H01S 3/139* | (2006.01) |
| *G01J 3/42* | (2006.01) |

(52) U.S. Cl.
CPC ............. *G01N 21/255* (2013.01); *G01J 3/28* (2013.01); *G01N 21/39* (2013.01); *H01S 3/1392* (2013.01); *G01J 3/42* (2013.01)
USPC ............................ 356/437; 356/326; 250/573

(58) Field of Classification Search
CPC .............. G01N 21/1702; G01N 21/39; G01N 2021/399; G01N 2021/391; G01J 3/42; G01J 3/28; H01S 3/1392
See application file for complete search history.

(56) References Cited

U.S. PATENT DOCUMENTS

| | | | |
|---|---|---|---|
| 5,528,040 A | 6/1996 | Lehmann | |
| 5,912,740 A | 6/1999 | Zare et al. | |
| 6,377,350 B1 | 4/2002 | Paldus et al. | |
| 6,466,322 B1 * | 10/2002 | Paldus et al. | 356/437 |
| 6,859,284 B2 | 2/2005 | Rella et al. | |
| 7,106,763 B2 | 9/2006 | Tan et al. | |
| 7,259,856 B2 | 8/2007 | Kachanov et al. | |
| 7,535,573 B2 * | 5/2009 | Kachanov et al. | 356/454 |
| 7,538,881 B2 | 5/2009 | Ye et al. | |
| 7,646,485 B2 * | 1/2010 | Tan | 356/437 |
| 7,813,886 B2 | 10/2010 | Tan | |
| 8,264,688 B1 * | 9/2012 | Tan | 356/437 |
| 8,665,442 B2 | 3/2014 | Koulikov et al. | |
| 2005/0052653 A1 | 3/2005 | Fidric | |
| 2006/0232779 A1 * | 10/2006 | Shaw | 356/436 |
| 2009/0066956 A1 * | 3/2009 | Tan | 356/437 |
| 2014/0192347 A1 * | 7/2014 | Koulikov et al. | 356/72 |

FOREIGN PATENT DOCUMENTS

WO  WO 2005/108939  11/2005

OTHER PUBLICATIONS

Schulz et al., "Frequency-matched cavity ring-down spectroscopy", 1998, pp. 523-529, Chemical Physics Letters v297.

* cited by examiner

*Primary Examiner* — Hoa Pham
(74) *Attorney, Agent, or Firm* — Lumen Patent Firm (57) ABSTRACT

For cavity enhanced optical spectroscopy, the cavity modes are used as a frequency reference. Data analysis methods are employed that assume the data points are at equally spaced frequencies. Parameters of interest such as line width, integrated absorption etc. can be determined from such data without knowledge of the frequencies of any of the data points.

22 Claims, 8 Drawing Sheets

REGULAR, STABLE OPTICAL FREQUENCY SCALE FOR CAVITY ENHANCED OPTICAL SPECTROSCOPY

CROSS REFERENCE TO RELATED APPLICATIONS

This application claims the benefit of U.S. provisional patent application 61/833,807, filed on Jun. 11, 2013, and hereby incorporated by reference in its entirety.

FIELD OF THE INVENTION

This invention relates to optical spectroscopy.

BACKGROUND

Spectroscopic measurements of quantities of interest (e.g., gas concentration) often rely on spectroscopic measurements at several frequencies. One common example is determination of gas concentration from a measured spectral absorption line of the gas. Here the integrated absorption over the spectral line can be used to determine the gas concentration.

Cavity enhanced optical spectroscopy makes use of an optical resonator to improve instrument performance. Cavity ringdown spectroscopy (CRDS) is one such method, where cavity energy decay times (i.e., cavity ringdown times) are measured in order to determine the absorption provided by a sample. In such instruments, it is important to consider the effect of the cavity modes on spectral absorption data. For example, in CRDS two operating modes have been considered in the art.

In the first CRDS operating mode, the optical source frequency is held at a nominally fixed value and the length of the cavity is varied such that cavity modes sweep through the source frequency, thereby generating ringdown events at the fixed source frequency. This operating mode can be referred to as a swept cavity mode. Spectral data in the swept cavity mode is obtained by tuning the source to the desired frequencies and sweeping the cavity length long enough at each of these source frequencies until sufficient data has been collected.

In the second CRDS operating mode, the cavity length is held at a nominally fixed value and the frequency of the source is varied such that the source frequency sweeps through one or more of the cavity mode frequencies, thereby generating ringdown events at the cavity mode frequencies. This operating mode can be referred to as a swept source mode. A single source frequency sweep in this mode provides absorption data points at frequencies that are spaced by the free spectral range (FSR) of the cavity. Measures to increase resolution in this mode have been employed. For example, the cavity length can be changed between successive source frequency sweeps such that frequency resolution is improved.

In either case, the resulting raw data for this kind of measurement generally has data points that are measurements at various frequencies (e.g., $(\nu, \alpha(\nu))$ pairs, where $\nu$ is frequency and $\alpha(\nu)$ is absorption at that frequency). Errors in the frequency $\nu$ of these data points can undesirably reduce the accuracy of the final determination of gas concentration.

It would be an advance in the art to provide spectroscopic methods that are less reliant on accurate frequency values in absorption data.

SUMMARY

The main idea of the present approach is to use the cavity modes as a quasi-frequency reference. More specifically, the cavity is constructed to passively provide sufficient frequency stability that:

1) for any single ringdown spectrum acquisition, which can be referred to as a spectrogram, the cavity frequencies are equally spaced by the FSR.
However,
2) from one spectrum acquisition to another, the cavity frequencies can change, although the FSR remains (approximately) constant.

Thus the cavity defines a frequency comb. The comb is substantially fixed in position during acquisition of a spectrogram, but the phase of the comb can drift in frequency space over time between spectrogram acquisitions.

Raw spectrograms are processed to provide outputs (e.g., concentrations, concentration ratios, etc.) using methods that do not need an absolute frequency scale for the data, but instead merely assume the data points are equally spaced in frequency (by the FSR, which often doesn't have to be known).

Figure 1:
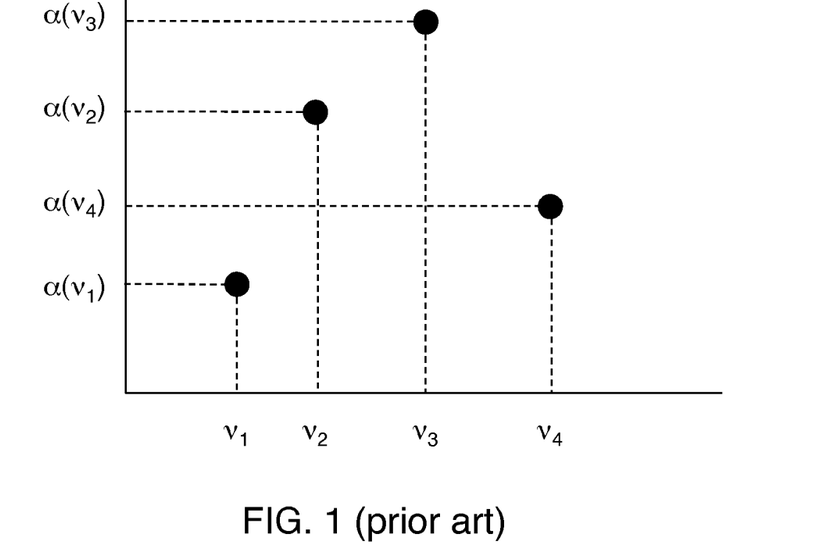
FIG. 1 schematically shows conventional spectral absorption data.
Figure 2:
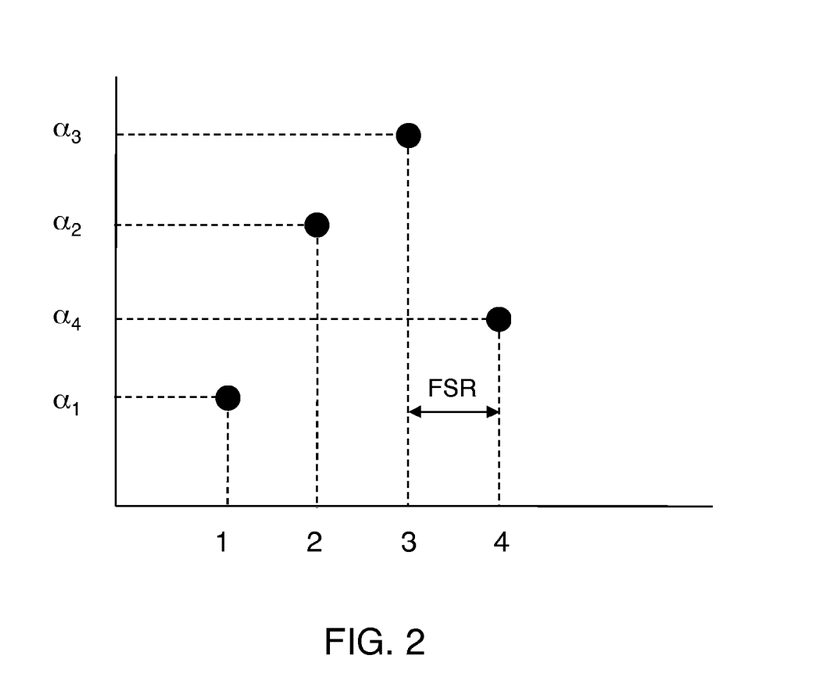
FIG. 2 schematically shows spectral absorption data as utilized in embodiments of the invention.

FIGS. 1 and 2 schematically illustrate this point. FIG. 1 shows conventional spectral absorption data, where each data point has an absorption value (e.g., $\alpha(\nu_1)$) and an associated frequency (e.g., $\nu_1$). FIG. 2 shows spectral absorption data as considered in the present work. Here each data point has an absorption value (e.g., $\alpha_2$) and an associated index (e.g., 2) that identifies the associated cavity mode. No frequency values for individual data points are considered or available in such a data set. Instead, as indicated above, it is assumed that the cavity is sufficiently stable during data acquisition that it defines a fixed comb of equally spaced frequencies.

We have found, surprisingly, that for many purposes it is not necessary to have $(\nu, \alpha(\nu))$ data points as in FIG. 1, and instead it suffices to have data as in FIG. 2. This discovery can be better appreciated by considering the computation of integrated spectral absorption from raw data. A conventional approach for this would be to perform measurements at points that are spaced significantly closer to each other than the line width of the feature being measured, e.g., as shown on FIG. 3. Numerical integration of such data would provide a reasonable estimate of the integrated absorption.

Attempting to obtain accurate integrated absorption results for data as in FIG. 2 would therefore appear to face two main obstacles: 1) for practical cavity dimensions, the frequency resolution provided by the cavity FSR tends to be comparable to line widths of feature of interest, which would appear to be inadequate resolution; and 2) knowledge of the frequencies would appear to be essential to compute the spectrally integrated absorption.

Figure 4:
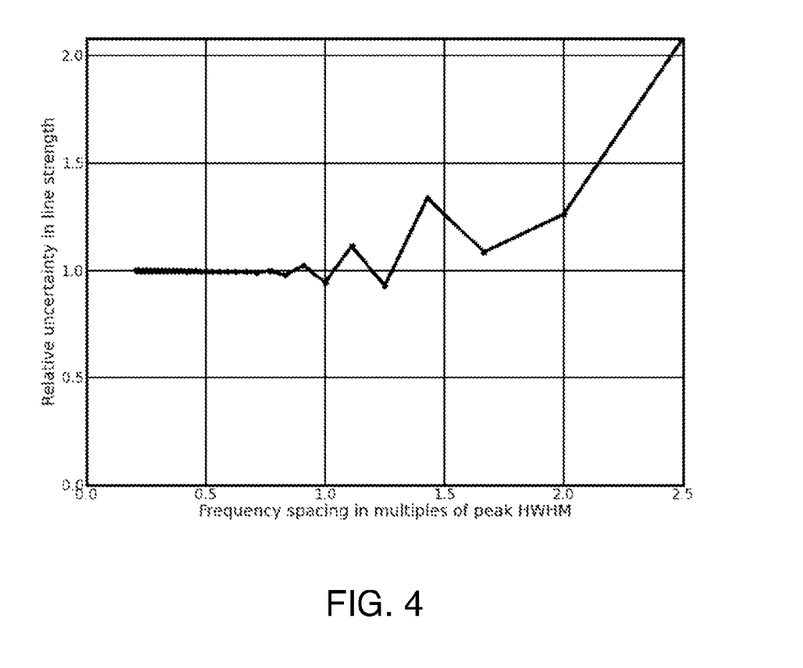
FIG. 4 shows an example of the effect of frequency resolution on parameter accuracy.

FIG. 4 shows an exemplary answer to the first problem identified above. For a spectral line of a given width, (as measured by its half-width at half maximum, denoted by HWHM), FIG. 4 shows how well its strength may be determined by distributing a fixed total number of absorption measurements amongst a whole number of uniformly spaced frequencies ranging from −5HWHM to +5HWHM around the peak. Once the spacing is comparable to the HWHM, there is little to be gained by using more finely spaced frequencies.

The answer to the second problem identified above is to avoid the use of numerical integration to determine integrated absorption. Instead, a line shape model is fitted to the data, assuming data points equally spaced in frequency, and the integrated absorption is determined from the fitting parameters (such as amplitude, line width, etc.). Such fitting can give an accurate absolute value for integrated absorption if the cavity FSR is known, and can give an accurate relative value of integrated absorption if the cavity FSR is not known. Thus the only frequency value that is used is the FSR, and even that minimal level of frequency information is not needed in all cases.

As described in greater detail below, the main motivation for this approach is that relying on frequency values in the data (as in FIG. 1) means that inaccurate frequency values will introduce corresponding errors in the final results such as integrated absorption. As a practical matter it is very difficult and costly to ensure sufficient accuracy for these frequency values. Avoidance of such cost and difficulties is the main advantage of the present approach.

DETAILED DESCRIPTION

In section A, some general principles relating to embodiments of the invention are considered. Section B is an extended example where these principles are considered in connection with cavity ring-down spectroscopy.

A) General Principles

Figure 5:
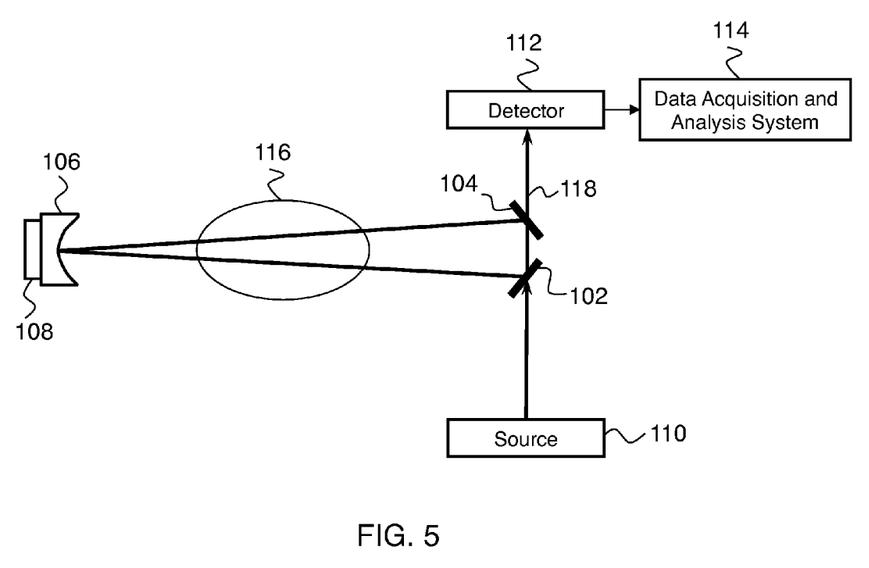
FIG. 5 shows an exemplary system suitable for practicing embodiments of the invention.

FIG. 5 shows an exemplary system for cavity enhanced spectroscopy suitable for practicing embodiments of the invention. Exemplary cavity enhanced spectroscopy methods include, but are not limited to: cavity ringdown spectroscopy, cavity enhanced absorption spectroscopy, and integrated cavity output spectroscopy. An optical resonator formed by mirrors 102, 104 and 106 defines a first set of cavity modes having a free spectral range (FSR). The optical resonator is configured to include a sample 116 for analysis, and is also configured to passively provide relative frequency stability of the first set of cavity modes of 10% or less of the FSR in a time period of about 1 second. More preferably, the relative frequency stability of the first set of cavity modes is 1% or less of the FSR in a time period of about 1 second. Still more preferably, the relative frequency stability of the first set of cavity modes is 0.1% or less of the FSR in a time period of about 1 second. Most preferably, the relative frequency stability of the first set of cavity modes is 0.01% or less of the FSR in a time period of about 1 second. Preferably, the optical resonator is disposed in an environment having actively stabilized temperature and pressure. Improving the frequency stability of the cavity increases the accuracy of the assumption of equally spaced frequencies that is made in data analysis.

Preferably, the first set of cavity modes are fundamental TEM00 modes. Alternatively, the first set of cavity modes can include one or more higher order transverse modes. Preferably, the optical resonator has a confocal geometry, such that frequency combs relating to different transverse modes are substantially aligned with each other. The optical resonator can have any optical or geometrical configuration suitable for use in connection with cavity enhanced spectroscopy, including but not limited to: standing wave resonator and ring resonator.

An optical source 110 is configured to deliver optical radiation to the optical resonator. In some embodiments, it is preferred for the optical source to provide relative frequency stability of the optical radiation of 10% or less of the FSR in a time period of about 1 second. In other embodiments, it is preferred for the optical source to provide relative frequency precision of the optical radiation of 10% or less of the FSR in a time period of about 1 second. A stable optical source can be used without needing a wavelength monitor, while a precise but unstable source can be used in connection with a wavelength monitor. A detector 112 is configured to receive an absorbance signal 118 from the optical resonator that is responsive to optical absorption in the sample. Optionally, the position of one or more cavity mirrors can be adjustable (e.g., piezoelectric transducer 108 on mirror 106).

In operation, data acquisition and analysis system 114 collects spectrograms from the sample 116 by sweeping a frequency of the optical source 110 through two or more frequencies of the first set of cavity modes and recording the absorbance signal. An analysis output from the spectrogram is computed by assuming that data points in the spectrogram are evenly spaced in frequency, without any reference to absolute frequencies of the data points.

Sweeping a frequency of the optical source through two or more frequencies of the first set of cavity modes can include dithering the frequency of the optical source around frequencies of two or more selected cavity modes to obtain one or more raw measurements at each of the selected cavity modes. The selected cavity modes can have equal numbers of raw measurements or different numbers of raw measurements.

Frequency control of the optical source can be used to facilitate tuning the frequency of the optical source to align with two or more of the first set of cavity modes when collecting spectrogram. In cases where the optical source is a semiconductor laser, the frequency control of the optical source can include both current control and temperature control.

Computing an analysis output can include determining an integrated absorption by fitting a spectral line shape model to the spectrogram. The analysis output can be a spectrally integrated concentration, an isotopic ratio, and/or a spectral line width of an analyte line.

Figure 10:
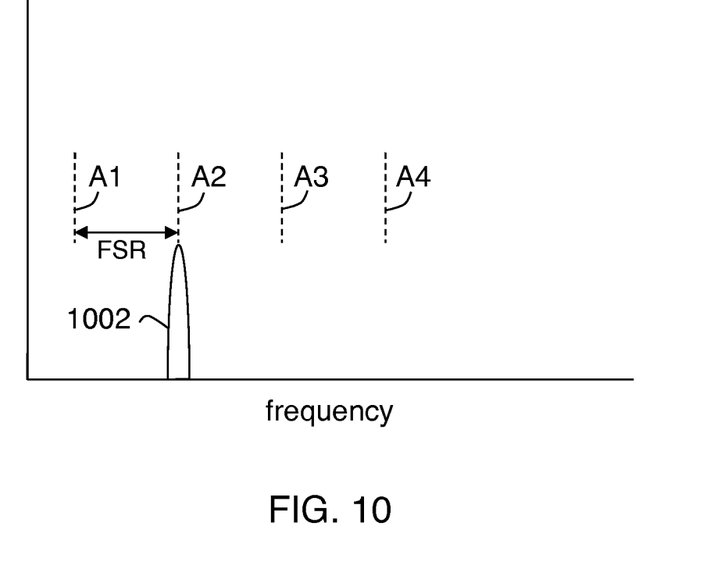
FIG. 10 shows the effect of locking a comb of cavity modes to a frequency reference.
Figure 11:
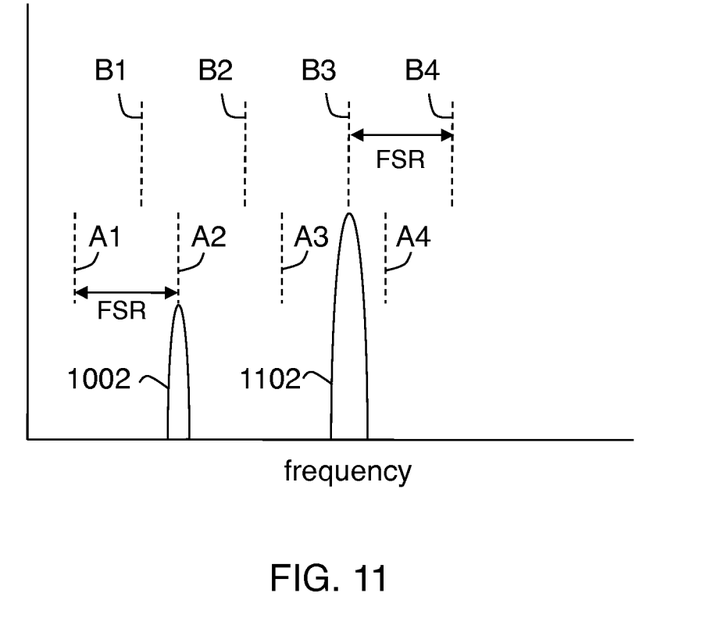
FIG. 11 shows the effect of locking two distinct combs of cavity modes to two frequency references.

The optical path length of the cavity can be controlled to align the cavity mode frequency comb to a frequency reference. Such a reference can be a spectroscopic feature of the sample. FIG. 10 shows an example. Multiple frequency references can be employed. For example, an optical path length of the optical resonator can be adjustable to two or more values in operation to define at least a second set of cavity modes distinct from the first set of cavity modes. If two or more sets of cavity modes are defined, they can each have their own frequency references. For example, the first set of cavity modes can be locked to a first frequency reference, and the second set of cavity modes can be locked to a second frequency reference. Spectroscopic features of the sample can provide multiple frequency references. FIG. 11 shows an example of this.

B) Exemplary CRDS Design Considerations

B1) Introduction

The cavity ring-down technique is an exceptionally sensitive means to determine the loss of a high-finesse optical cavity, including any optical absorbers present in the beam path defined by the cavity. The ring down method is combined with a tunable light source in cavity ring-down spectroscopy (CRDS). Measurements of cavity loss at multiple frequencies in the neighborhood of a molecular absorption line or lines permit the detection of trace amounts of absorbing species in a gas sample enclosed in the cavity. In order to derive a quantitative measurement of the concentration of the absorbing species from the ring-down loss, accurate and stable knowledge of the optical frequencies at which the CRDS measurements were made is usually regarded as being essential.

We describe a means of injecting light from a laser into an optical cavity which has the advantages of considerable freedom in choosing the optical frequencies at which data points are acquired and high speed of data acquisition, while using the ring-down cavity itself as a very stable local frequency standard. This approach exploits the precision with which the distribution of cavity resonance frequencies is known when the length of the cavity is kept fixed, in order to improve the stability of each absorption measurement. Accurate frequency values for absorption data points are not necessary. We show how the spectra acquired with the CRDS spectrometer, operating in this manner, can be analyzed to yield precise, quantitative measurements of molecular concentrations and concentration ratios, with excellent stability over long time intervals.

B2) Spectroscopic background

In wavelength-scanned CRDS (WS-CRDS), the quantity that is directly measured is the cavity loss and measurements are made at multiple optical frequencies to construct a loss spectrum. The loss spectrum of the empty cavity can be determined from ancillary measurements and the remaining loss is assumed to be due to linear absorption by the gas sample filling the cavity. Linear absorption in this context means absorption that follows Beer's law, $$I(z)=I_0\exp[-\alpha(v)z]$$

where $I_0$ is the optical intensity at $z=0$ of a uniform beam of light propagating in the positive z direction, $I(z)$ is the intensity after propagating the distance z in the uniform absorbing medium, and $\alpha$, which is a function of optical frequency $v$, is the absorption coefficient. In the linear regime $\alpha$ is proportional to the number density of absorbing molecules in the cavity, and this proportionality allows one to deduce the concentration of absorbing molecules in the gas sample from the measured cavity loss.

Figure 3:
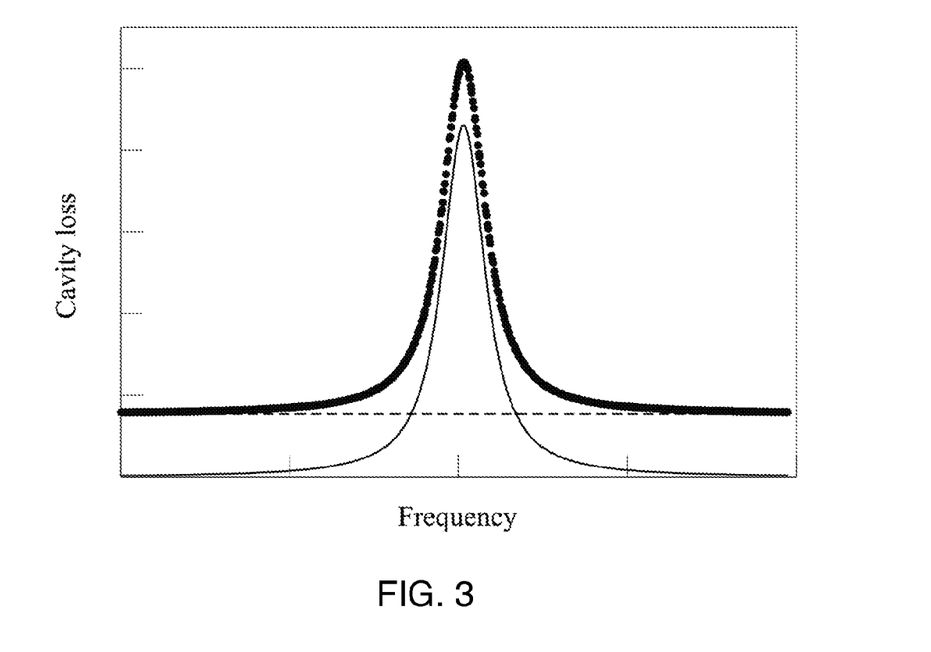
FIG. 3 is an example of absorption data.

An example of an absorption spectrum for a single, isolated spectral line is illustrated in FIG. 3. Here points are measured cavity loss values, the dashed curve is the empty cavity loss measured separately, and the solid curve is the loss due to a single spectral line. In this example, the frequency dependence of the molecular absorption is accurately described by the Galatry function of spectral line shape theory. The frequency spread of the line in FIG. 3 is determined by the conditions in which the absorbing molecules find themselves: the temperature, pressure, and composition of the surrounding gas. Regardless of the line shape, the integrated absorption, $$\int_0^\infty \alpha(v)\,dv,$$

is the quantity which is proportional to molecular number density. Other measures of molecular absorption, such as the absorption at a specific frequency, depend on the line shape as well as the molecular number density. Because the integrated absorption is the quantity most directly related to molecular number density, it is especially well suited to serve as the basis of a spectroscopic determination of the composition of a gas sample. However, the computation of integrated absorption from measured WS-CRDS data depends crucially on how well one knows the frequencies of the measured loss values. Errors in the frequencies $v$ at which the $\alpha(v)$ were measured directly affect the integrated absorption.

Note that as a practical matter, we do not attempt a mathematical or numerical quadrature to find the integrated absorption. Rather we use the method of least-squares fitting of measured spectral data to a model with adjustable parameters. In this procedure we derive a spectral model from careful measurements of samples of known composition. The spectral model includes the empty cavity loss and the absorption from the species to be quantified as well as other molecules than can be in the samples to be analyzed. Non-resonant absorption from strong spectral lines outside the frequency range of the measurements may also need to be included. In its final form the spectral model is a mathematical expression in terms of known functions which incorporates a number of adjustable parameters. For instance, the spectrum of FIG. 3 might be modeled as the sum of a baseline with a slope and offset and a term $AG(v)$, where $G(v)$ is a Galatry function normalized such that $$\int_0^\infty G(v)\,dv = \sqrt{\pi},$$

and A is a coefficient that describes the amplitude of the absorption feature. When analyzing the loss spectrum of an sample of unknown composition, a number of parameters including the coefficient A and possibly the Galatry parameters that determine the shape of the spectral line, are adjusted to minimize the sum of squares of the deviations of the model from the observed spectrum. The model spectrum with optimized adjustable parameters is then taken to be the best estimate of the true spectrum of the sample. Since the Galatry function G is defined to have area $$\sqrt{\pi},$$

the coefficient A is, except for unimportant constant factors, the same as the integrated absorption. An important consequence of the least-squares fitting method is that the ring-down measurements can be made at any set of optical frequencies that provides enough spectral information to constrain all the adjustable parameters in the model. Measurements do not have to be made at frequency intervals small compared to the widths of the absorption lines. For instance, although the finely spaced spectrum shown in FIG. 3 may present a human observer with the pleasing illusion of continuity, far fewer discrete frequencies are actually needed to determine the center frequency, width, and amplitude of the spectral line, as seen on FIG. 4.

B3) Improvement of the Frequency Scale for WS-CRDS

Stability and linearity of the frequency axis are directly related to the precision and drift of the WS-CRDS analyzer. Although frequency metrology is capable in principle of extraordinary precision through the use of optical frequency combs or atom-stabilized reference lasers, such technologies are much too complex and expensive to be used in field-deployable, relatively inexpensive instruments. Consequently, frequency assignments for the CRDS have in the past been made by independent calibration of the laser frequency as a function of operating temperature and current, or by an auxiliary measurement with a dispersive element such as a wavelength monitor (WLM). Both of these methods suffer from drift on time scales longer than a few minutes. We have now implemented a new technique that improves frequency precision and stability by using the CRDS cavity itself as the ultimate frequency reference.

A high-finesse optical cavity exhibits very narrow resonances at discrete frequencies labeled by transverse and longitudinal mode numbers. We take care to align the cavity and laser such that only the lowest-order transverse mode, the $TEM_{00}$ mode, is excited. The cavity resonance frequency thus depends only on the longitudinal mode number, equal to the optical phase acquired by the light beam during one round trip of the cavity, in units of $2\pi$ radians. This means that, neglecting the tiny effect of dispersion over typical CRDS frequency ranges, the modes of the cavity are equally spaced in frequency. The mode spacing is referred to as the free spectral range (FSR) of the cavity. If we choose to express frequency in units of wavenumber, $k=v/c$ where c is the speed of light in vacuum, the free spectral range is simply $$FSR=1/L$$

where L is the optical path length of the resonant mode. For a typical cavity, L=48 cm, which leads to a free spectral range that is somewhat smaller than the line width of the molecular absorption lines under typical spectroscopic conditions.

The regular comb of longitudinal modes of the CRDS cavity itself provides a frequency measuring stick that is extremely precise and stable, without adding at all to the cost or complexity of the CRDS spectrometer. By manufacturing the cavity from a low temperature coefficient material and stabilizing the temperature of the cavity, the mechanical length of the cavity mode can be kept very nearly constant. Invar, for instance, has temperature coefficient of expansion on the order of $10^{-6}$/K, and it is practical to stabilize the cavity temperature to 0.01-0.1 K, so the mechanical length of the cavity an be made stable to about $10^{-8}$-$10^{-7}$. By stabilizing the pressure of the gas in the cavity (e.g., air) the index of refraction of the medium in the cavity can be kept very nearly constant. Assuming the cavity is filled with air at an operating pressure of 140 Torr, the relative change of the cavity FSR with pressure is $2.6\times10^{-7}$/Torr. Pressure stabilization of 0.01-0.1 Torr is practical, so pressure changes contribute on the order of $10^{-8}$ to the cavity FSR. When the optical path length of the cavity is kept constant, spectra acquired at frequencies separated by integral multiples of the free spectral range can be fit to a model of absorption versus optical frequency, as described above, with frequency values that are precise and stable over long periods of time. Consequently the ultimate precision of the CRDS analyzer is improved.

To exploit the stability of the CRDS cavity as an optical frequency standard we have devised a new mode of operation for the WS-CRDS analyzer. Minimally, a means of setting and determining the frequency of the laser at the time of each ring-down is required. So long as the resolution of this determination is better than the separation between cavity resonances, it is possible to classify each ring-down measurement as occurring at the frequency of a particular resonance, and hence to determine its position in the spectrum. The method of setting the frequency of the laser so as to collect data efficiently and with sufficiently high repetition rate to allow enough measurements to be made to achieve the desired levels of precision is more challenging, and constitutes a significant aspect of this work. The ability to specify a list of frequencies at which the data are to be collected, and to specify the number of ring down events that are to be collected at each of these frequencies are key to optimizing the data collection process for a given measurement.

Figure 6:
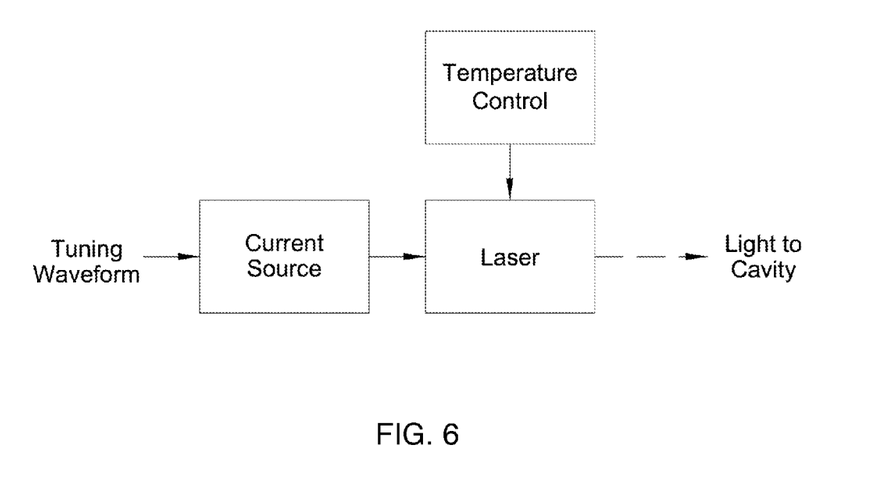
FIG. 6 is a simplified block diagram of laser control.
Figure 7:
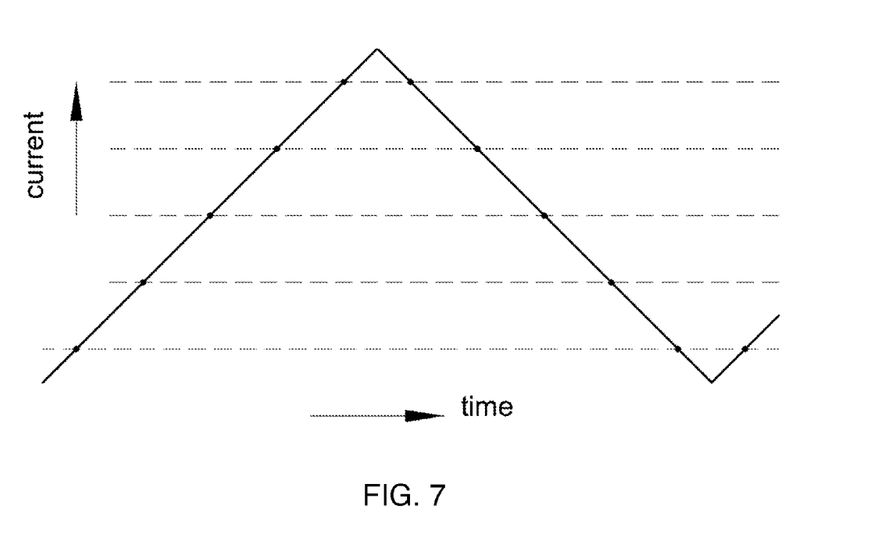
FIG. 7 schematically shows an example of laser tuning for CRDS.

Setting the frequency of a laser involves adjusting various physical parameters, depending on the details of its construction. For the purposes of this discussion, the laser temperature and current will be used as representative examples of such parameters as these are appropriate for semiconductor distributed feedback lasers. FIG. 6 is a block diagram of a portion of the laser control subsystem of a cavity ring down spectrometer using such a laser. The laser injects light into an optical cavity, and the laser temperature and current are adjusted to tune the laser to the desired frequency. When the intensity in the cavity reaches a predetermined value, a trigger signal is generated to turn off the optical injection and initiate a ring down. In the simplest approach, the laser frequency is tuned over the range of interest, for example by driving the laser current with a triangular tuning waveform of the appropriate amplitude (see FIG. 7). Assuming that the laser temperature is kept constant, its frequency will vary with the current, and the optical cavity will fill with sufficient light to allow a ring down to be initiated from time to time. In FIG. 7, the laser current values which cause the laser frequency to coincide with a cavity resonance are shown as dashed lines. Each time the laser current crosses such a line, there is an enhanced probability of cavity filling, and a ring down can occur if the amount of light within the cavity is sufficiently large. Such times are indicated by dots. The slope of the tuning waveform determines the rate at which the laser frequency is varied and in order to efficiently fill the cavity, this rate must be limited so that the light is quasi-monochromatic on the timescale of the cavity filling. In such a system, the acquisition rate will be slow, because for most of the time, the laser frequency falls between the cavity resonances during which time no filling occurs.

Figure 8:
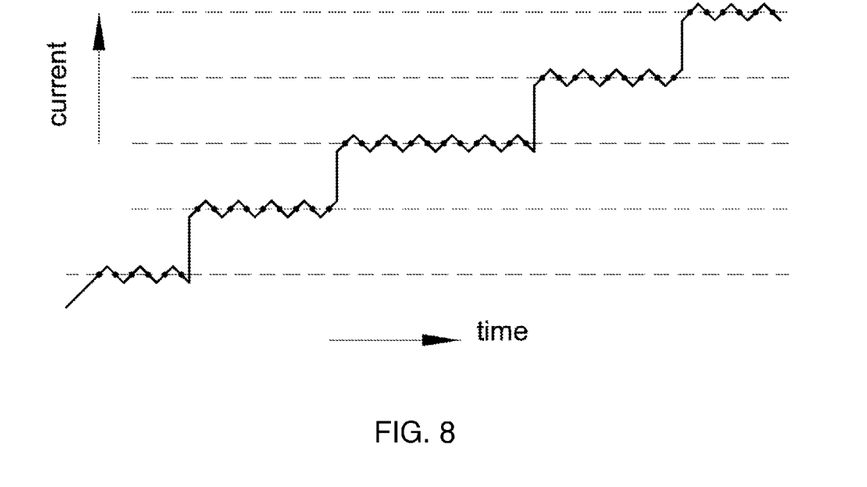
FIG. 8 schematically shows an improved approach for laser tuning for CRDS.

An improvement to the above approach is to modify the tuning waveform so that the laser does not spend much of the time tuned to frequencies at which the cavity is not resonant. If the value of the laser current is recorded at the time a successful ring down occurs, further ring downs may be collected at the same frequency by varying the current in a narrow range (dithering) around this recorded value (see FIG. 8). It is still important to keep the slope of the waveform small, to maintain filling efficiency, but so long that the range is limited to a small fraction of the separation between cavity resonances, the rate at which ring down events occur can be much larger than with the simple approach. In order to tune the laser to a different cavity resonance while maintaining the large ring down rate, the current needs to be changed quickly (shown by the vertical lines) so that it is close to the value needed to achieve the new resonant frequency before it is swept more slowly to achieve good cavity filling at this frequency. The various laser currents needed to move between cavity resonances may be predetermined and stored in a lookup table for subsequent use.

Several problems become apparent when we remember that laser current is not the only quantity that determines the frequency. If the laser temperature is not constant, the current required to bring the laser frequency into coincidence with a cavity resonance is not constant and so varying the laser current in a small range with the expectation of keeping the laser frequency correspondingly close to a cavity resonance will fail. The effect of a varying laser temperature can be visualized by imagining the dashed lines in FIGS. 7 and 8 as no longer being horizontal, but rather moving up and down as the temperature changes. If ring downs are initiated by turning off the laser current, followed by subsequently turning the laser on again to initiate a new acquisition cycle, this process results in significant temperature fluctuations and gradients within the laser which are difficult to stabilize against, since they occur at much faster timescales than are accessible to a typical thermal controller. Similarly, jumping between successive cavity modes using precomputed currents is not feasible when the laser temperature fluctuates unpredictably.

One approach to overcoming these problems is to avoid processes that change the temperature of the laser, so that its value can be maintained more precisely constant. For example, an external modulator may be used to turn off the optical injection into the cavity, rather then turning the laser off by removing or reducing the current. Although effective, the additional cost of such a modulator may render this solution less desirable for many applications. Thus it is helpful to have ways to control the laser in cases where the laser is turned off to initiate ringdowns. Another point to consider is that detuning the laser from the resonance removes much of the light from the cavity, but it doesn't eliminate it completely, and the light that remains can beat with the light in the cavity to create a time-varying signal that leads to noise on the measurement of the ringdown time. Thus detuning the laser may not be an appropriate way to initiate ringdowns, even though it does have the advantage of not significantly altering the laser temperature.

Figure 9:
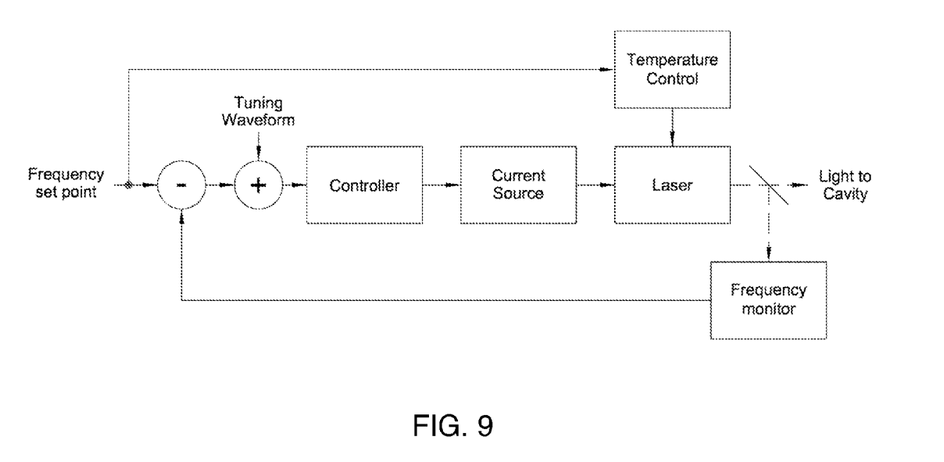
FIG. 9 is a block diagram of temperature and current control of a laser using a frequency monitor.

Another approach is to use a frequency measuring device such as described in U.S. Pat. No. 7,813,886 within a feedback loop to adjust the laser current (as shown in FIG. 9). The difference between the frequency set point and the measured frequency is the error signal, and this is used to adjust the laser current so that the laser frequency remains close to the desired value, even in the presence of laser temperature fluctuations or other external disturbances. A block implementing an algorithm such as a PID (proportional, integral and derivative) controller may usefully be introduced in order to take into account the dynamics of the feedback loop.

By specifying the frequency set points to be a collection of frequencies separated by multiples of the free spectral range of the cavity, the laser can be tuned close to the cavity resonances in a range of frequencies that generate the desired spectrum. Since the laser current can be adjusted rather quickly, and the laser frequency responds to such adjustments with very small delay, the time response of the feedback loop can be made much faster than any temperature changes. The slow tuning of the laser required to bring its frequency into precise resonance with the cavity can now be carried out by adding a triangular tuning waveform to the set point of the control loop (or equivalently to the error signal).

The method outlined above of recording the value of the tuning waveform at the time of a successful ring down event and subsequently dithering the waveform about this value is again useful for generating a rapid succession of ring down events at a single frequency. If the set point of the feedback loop is adjusted to be close to another cavity resonance, ring down events at the new frequency will occur so long that the amplitude of the triangular waveform is large enough to sweep the laser frequency through the resonance. If this is not the case, it is possible to find the new resonant frequency simply be increasing the amplitude of the tuning waveform until a ring down does occur and then switching back into the rapid dithering about this value. By introducing the tuning waveform at this position in the feedback loop, it is necessary to ramp its value over at most a single cavity free spectral range in order to bring the laser and the cavity into resonance.

A simple heuristic for switching from dithering to ramping is to do so if a ring down has not been detected for more than some length of time. With careful adjustment of the amplitude of the triangular waveform, so that it exceeds the imprecision inherent in the frequency measuring device, it is possible to make the transition to ramping occur infrequently, allowing a continuously high data acquisition rate.

Since the feedback loop now adjusts the laser current to the correct value in order to achieve a desired laser frequency, we can adjust the laser temperature so that the range of adjustment required for the laser current is reduced. This can be achieved by storing the laser temperature required to produce a given frequency when the current is at some nominal value. When it is desired to generate a particular frequency, the laser temperature control system is instructed to change the laser temperature to that value, as indicated by the line in FIG. 9 which links the temperature control block to the frequency set point. Even as the temperature is approaching the set point (on the relatively slow timescale of the thermal control loop), the laser current will be adjusted by the feedback loop to produce the correct frequency. All during this time, rapid ring down acquisition can take place, as the frequency is well controlled. Since the laser frequency can typically be tuned over a much wider range by varying the temperature than by varying the current, this allows the system to access the entire frequency range available to the laser.

Although a frequency monitor is used within the control loop, it is important to note that the frequencies at which the data are collected are still determined by the cavity resonances. Any inaccuracy or drift in the frequency monitor does not affect the quality of the measurement, so long that these do not compromise our ability to assign each ring down unambiguously to a specific resonance. Any long-term drifts can usually be compensated for by using spectroscopic information in the collected spectra, such as the frequencies of known absorption features.

The methods described above are generically referred to as laser current tuning (LCT) modes to emphasize that the laser current is used to bring the laser frequency into coincidence with a cavity resonance. With the appropriate refinements, the procedure produces a rapid sequence of ring down events for a prescribed sequence of longitudinal modes of the cavity, with the cavity length being held constant. In this way, a spectrum of cavity loss versus frequency is acquired with the property that all optical frequencies lie precisely on a comb with frequency spacing equal to the cavity FSR. If more than one molecular species is to be analyzed, it is possible to acquire a piecewise spectrum in which each spectral line of interest is covered by a comb of frequencies spaced by exactly one FSR, but the FSR-spaced pieces are shifted by an arbitrary frequency, by moving one mirror of the cavity with a piezoelectric translator (PZT). In this case each piece of the total spectrum has a stable frequency axis, by virtue of the stability of the cavity FSR, while the relative positions of the pieces are stable because they are tied to molecular absorption lines which have inherently well defined frequencies. It is also possible to use spectroscopic fitting to inform how the length of the cavity should be changed, if it is desired to align some cavity resonance with the peak of a specific spectral line, so that many points may be collected precisely at the peak, in order to measure better the value of the absorption.

B4) Analysis of Spectra Acquired in LCT Mode

After a spectrum of loss versus frequency has been acquired, it is analyzed by least-squares fitting to a spectroscopic model, as described above. The most important difference from conventional data analysis is that the optical frequencies associated with the ring-down measurements are constrained to be spaced by multiples of the cavity FSR. The free parameters that are adjusted in the fit typically include the line amplitude A, the line width, and the center frequency of the fitted spectral line. The line amplitude is used to derive the concentration of the species of interest in the sample. The measured center frequency can be used to ensure long-term stability of the frequency scale, even though there may be slow and undetected drifts in the temperature and pressure sensors that are used to stabilize the cavity. If the fitting procedure indicates that the experimentally observed ring-downs are displaced in frequency from the requested values, a small correction is applied to the PZT to adjust the mechanical length of the cavity accordingly. In this way the optical path length can be stabilized such that a specific longitudinal mode of the cavity always has a spectroscopically fixed frequency. The PZT adjustment is applied between periods when ring-down spectra are applied, so that each spectrum is acquired with optical frequencies on an FSR grid. FIG. 10 shows an example of the resulting alignment of the frequency comb having frequencies A1, A2, A3, and A4 with a frequency reference 1002, which could be an absorption peak in the sample.

This idea of locking frequency combs to frequency references can be extended to two (or more) frequency combs and references, as shown on FIG. 11. Here the cavity length can be controlled to define a first set of cavity modes A1, A2, A3 and A4 that is locked to a first frequency reference 1002. The cavity length can also be controlled to define a second set of cavity modes B1, B2, B3, and B4 that is locked to a second frequency reference 1102. Switching between these modes can be accomplished without removing the sample from the instrument, so the ability to sequentially use multiple different frequency references can be valuable for analyzing multi-component samples.

The use of the line amplitude together with the stabilization of the frequency axis by the LCT method greatly reduces the sensitivity of the analyzer to drift or instability in the pressure control of the sample. The reasoning is slightly different for analyzers intended for concentration measurements or for stable isotope analysis. Consider isotopic analysis first. In this case it is the ratio of isotopologues of a given molecule that is of interest, more than absolute concentration. Stabilizing the frequency axis allows reproducible measurements of line strengths over long time periods, and the ratio of line strengths provides a measurement of the isotopic ratio which is independent of the cavity pressure and therefore not affected by slow drifts in the cavity pressure sensor. The result is more reproducible measurements that can be averaged for long time periods, yielding better ultimate isotopic ratio precision. When measuring the concentration of a molecular species, drift in the pressure sensor degrades measurement reproducibility, because for a given sample composition the number density of the absorbing species in the cavity is proportional to pressure as known from the ideal gas law. The improved frequency axis provided by LCT is valuable for concentration measurements because it allows a more stable, reproducible measure of the spectral line width. Since collisional broadening of the spectral line is proportional to pressure, as is the number density of molecules in a gas sample, the line width information can be used to correct for drifts in cavity pressure, thus improving the long-term reproducibility of concentration measurements.

B5) Comparison of Experimental Data

Figure 12:
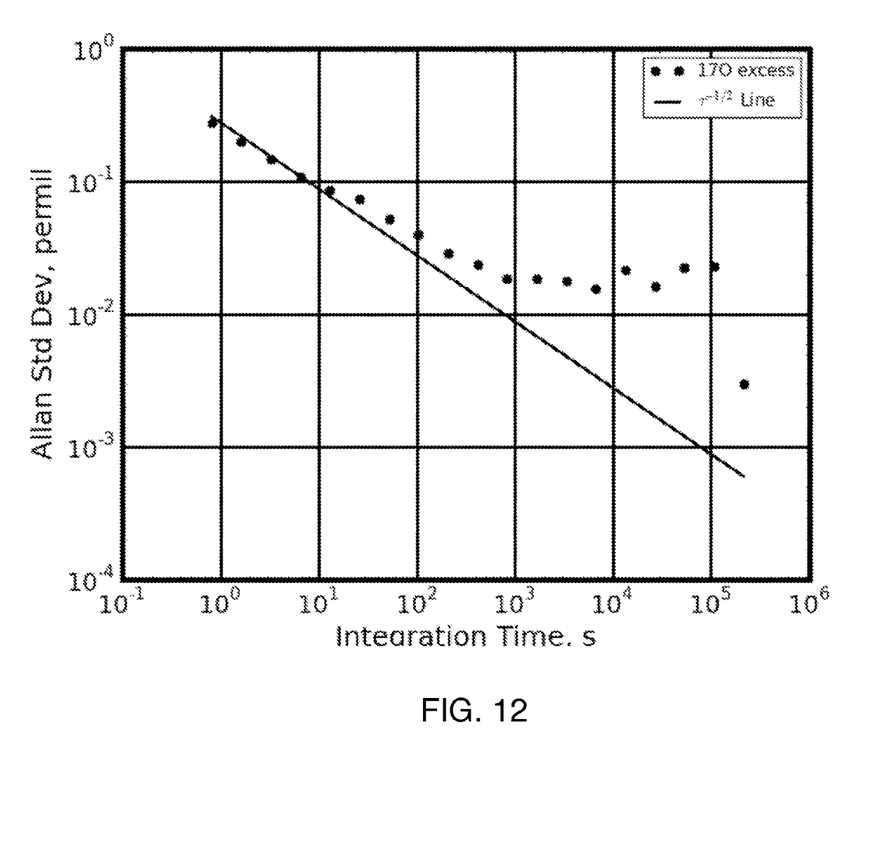
FIG. 12 shows Allan variance results for conventional CRDS.

The Allan variance provides a quantitative way of depicting the stability of a measurement method when it is used to measure repeatedly the same quantity. A wavelength scanned cavity ring down spectrometer was used to measure the relative isotopic abundance of the oxygen isotopes $^{16}O$, $^{17}O$ and $^{18}O$ in water vapor of constant composition. The analyzer was first configured to use cavity length tuning, in which the cavity length is adjusted to bring it into resonance with the laser. The laser frequency is adjusted using the frequency monitor alone as its reference. Data were collected for several days in order to determine how well the uncertainty would decrease as the measured results are averaged. FIG. 12 shows that the optimum precision achieved is about 20 per meg, after an averaging time of approximately 1000 s. Due to drifts in the system, further averaging does not improve the precision further.

Figure 13:
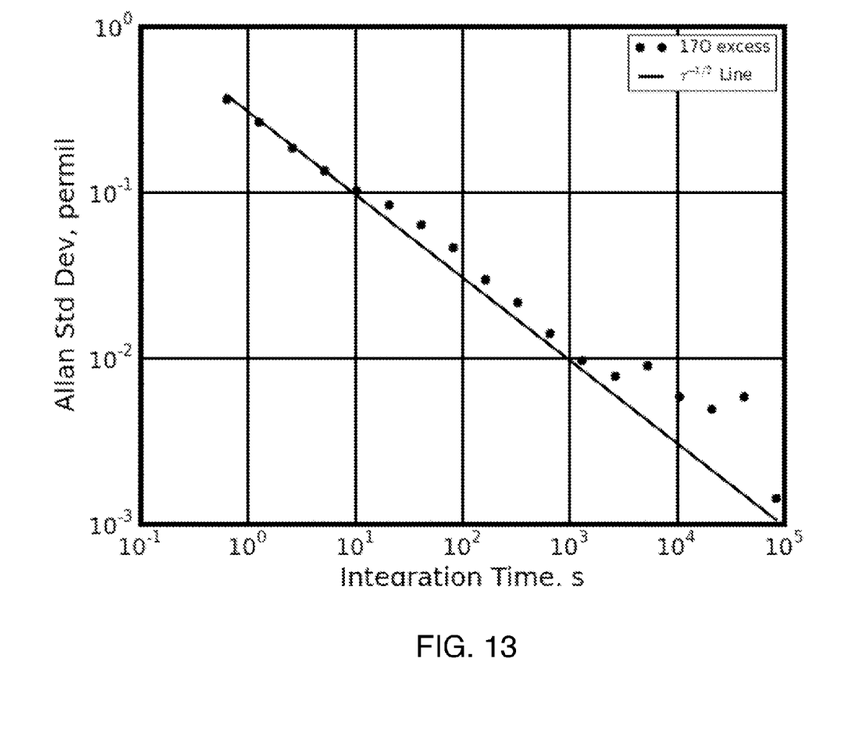
FIG. 13 shows Allan variance results corresponding to FIG. 12 when laser current tuning CRDS is employed.

When the analyzer was subsequently configured to use the enhanced laser current tuning method described above, so that the frequency axis is now calibrated using the equally spaced cavity resonances, the new Allan variance plot is as shown in FIG. 13. Averaging can now usefully be performed for timescales around 10,000 s resulting in higher precision of about 5 per meg.

B6) Conclusion

This work provides methods to:
1) Acquire WS-CRDS data using a spectrometer with a stable, high-finesse optical cavity and (optionally) an ancillary wavelength monitor, generating spectra for which the optical frequencies are directly related to the optical path length of the cavity while simultaneously permitting high measurement rate and flexible allocation of ringdown measurements at different wavelengths.
2) Analyze the WS-CRDS spectra so acquired to derive physically meaningful quantities, such as mixing ratios of gas species or isotopic ratios of specific molecules, in such a way as to minimize the sensitivity of the results to variations in the conditions under which the spectra were acquired.
3) Tune a laser successively to a collection of frequencies by altering one or more laser parameters such as the current and temperature, each of these frequencies being sufficiently close to a resonant frequency of an optical cavity that efficient optical injection can be achieved with high duty cycle.
4) Carry out the desired laser tuning with the aid of an ancillary wavelength monitor within a feedback loop.

The invention claimed is:
1. A method for performing cavity enhanced optical spectroscopy, the method comprising:
providing an optical resonator that defines a first set of cavity modes having a free spectral range (FSR) and which is configured to include a sample for analysis, wherein the optical resonator is configured to passively provide relative frequency stability of the first set of cavity modes of 10% or less of the FSR in a time period of about 1 second;

providing an optical source configured to deliver optical radiation to the optical resonator;

providing a detector configured to receive an absorbance signal from the optical resonator that is responsive to optical absorption in the sample;

collecting spectrograms from the sample by sweeping a frequency of the optical source through two or more frequencies of the first set of cavity modes and recording the absorbance signal; and computing an analysis output from the spectrogram by assuming that data points in the spectrogram are evenly spaced in frequency, without reference to absolute frequencies of the data points.

2. The method of claim 1, wherein the optical source is configured to provide relative frequency stability of the optical radiation of 10% or less of the FSR in a time period of about 1 second.

3. The method of claim 1, wherein the optical source is configured to provide relative frequency precision of the optical radiation of 10% or less of the FSR in a time period of about 1 second.

4. The method of claim 1, further comprising disposing the optical resonator in an environment having actively stabilized temperature and pressure.

5. The method of claim 1, wherein the sweeping a frequency of the optical source through two or more frequencies of the first set of cavity modes comprises dithering the frequency of the optical source around frequencies of two or more selected cavity modes to obtain one or more raw measurements at each of the selected cavity modes.

6. The method of claim 5, wherein the selected cavity modes have equal numbers of raw measurements.

7. The method of claim 5, wherein the selected cavity modes have different numbers of raw measurements.

8. The method of claim 1, further comprising providing frequency control of the optical source to facilitate tuning the frequency of the optical source to align with two or more of the first set of cavity modes during the collecting spectrogram.

9. The method of claim 8, wherein the optical source is a semiconductor laser and wherein the frequency control of the optical source comprises both current control and temperature control.

10. The method of claim 1, wherein the method for performing cavity enhanced optical spectroscopy comprises a method selected from the group consisting of: cavity ringdown spectroscopy, cavity enhanced absorption spectroscopy, and integrated cavity output spectroscopy.

11. The method of claim 1, wherein the first set of cavity modes are fundamental TEM00 modes.

12. The method of claim 1, wherein the first set of cavity modes include one or more higher order transverse modes.

13. The method of claim 1, wherein the optical resonator has a confocal geometry, whereby frequency combs relating to different transverse modes are substantially aligned with each other.

14. The method of claim 1, wherein the computing an analysis output comprises determining an integrated absorption by fitting a spectral line shape model to the spectrogram.

15. The method of claim 1, wherein the analysis output is a spectrally integrated concentration.

16. The method of claim 1, wherein the analysis output is an isotopic ratio.

17. The method of claim 1, wherein the analysis output is a spectral line width of an analyte line.

18. The method of claim 1, further comprising controlling the optical path length of the optical resonator to align one of the first set of cavity modes to a first frequency reference.

19. The method of claim 18, wherein the first frequency reference is determined from a first spectroscopic feature of the sample.

20. The method of claim 18, wherein an optical path length of the optical resonator is adjustable to two or more values in operation to define at least a second set of cavity modes distinct from the first set of cavity modes.

21. The method of claim 20, further comprising controlling the optical path length of the optical resonator to align one of the second set of cavity modes to a second frequency reference.

22. The method of claim 21, wherein the second frequency reference is determined from a second spectroscopic feature of the sample.

* * * * *